United States Patent [19]

Tsunekawa et al.

[11] Patent Number: 4,871,441
[45] Date of Patent: Oct. 3, 1989

[54] ION ACTIVITY MEASURING DEVICE

[75] Inventors: Yuzo Tsunekawa; Hikaru Tsuruta, both of Minami-ashigara; Takehiko Sato, Asaka, all of Japan

[73] Assignee: Fuji Photo Film Co., Ltd., Kanagawa, Japan

[21] Appl. No.: 326,428

[22] Filed: Mar. 17, 1989

Related U.S. Application Data

[63] Continuation of Ser. No. 133,503, Dec. 16, 1987, abandoned.

[30] Foreign Application Priority Data

Dec. 16, 1986 [JP] Japan ................................. 61-300545

[51] Int. Cl.$^4$ ........................................... G01N 27/30
[52] U.S. Cl. .................................... 204/409; 204/411; 204/416; 422/68; 422/69
[58] Field of Search ............... 204/409, 411, 412, 416; 422/68, 69

[56] References Cited

U.S. PATENT DOCUMENTS 4,684,445  8/1987  Seshimoto et al. ................. 204/1 T
4,789,435 12/1988  Seshimoto et al. ................. 204/1 T Primary Examiner—G. L. Kaplan
Attorney, Agent, or Firm—Jules E. Goldberg

[57] ABSTRACT

An improvement of a device for measuring ion activity in a liquid sample comprising at least a pair of ion-selective electrode sheets, liquid-guiding portions for guiding a reference liquid and a liquid sample to each active surface of the pair of ion-selective electrode sheets respectively, and a bridge for electrically connecting both liquids supplied on the electrode sheets to each other is disclosed. Each ion-selective electrode sheet is arranged in such a manner that the active surface of the ion-selective electrode is placed upside down and each liquid guiding portion comprises a horizontal passage for conveying the liquid sample or the reference liquid supplied from the outside in the horizontal direction to the position just below the active surface of the ion-selective electrode, the horizontal passage being formed in a lower position than the active surface of the ion-selective electrode; and the horizontal passage is provided with a porous distributor which is bent to protrude upwardly from the horizontal passage up to the position just below the active surface of the ion-selective electrode so that the liquid sample or the reference liquid conveyed to the porous distributor can be brought into contact with the active surface of the electrode.

6 Claims, 6 Drawing Sheets

ION ACTIVITY MEASURING DEVICE

This is a continuation of application Ser. No. 133,503, filed Dec. 16, 1987 and now abandoned.

BACKGROUND OF THE INVENTION

1. Field of the invention

The present invention relates to a device for measuring ion activity for the quantitative analysis of specific ion activity (or ion concentration) contained in an aqueous liquid, particularly a body fluid such as blood, urine or saliva, utilizing potentiometry.

2. Description of prior art

There has been known a device for measuring specific ion activity contained in a liquid sample of an aqueous liquid (e.g., tap water, river water, sewage or industrial drainage) and a body fluid (e.g., blood such as whole blood, plasma and serum, urine, or saliva) by using an ion selective electrode sheet.

A reference liquid and a liquid sample are spotted onto surfaces of ion-selective membranes, respectively, which are arranged on the top of at least a pair of ion-selective electrode sheets, and then potential difference between the ion-selective electrodes is measured under the condition that both liquids are electrically connected to each other by means of a bridge, so as to determine the ion activity of the liquid sample.

Examples of the ion activity measuring device employable in the method are described, for instance, in Japanese Patent Provisional Publications No. 52(1977)-142588 (corresponding to U.S. Pat. No. 4,053,381), No. 56(1981)-6148 (corresponding to U.S. Pat. No. 4,273,638) and No. 58-211648 (corresponding to U.S. Pat. No. 4,437,970).

In these devices, a pair of ion-selective electrode sheets are arranged in such a manner that ion-selective membranes are positioned on the upper side, and on the frame covering the ion-selective electrode are provided liquid receiving openings (openings for allowing introduction of a reference liquid and a liquid sample) A reference liquid and a liquid sample are spotted onto the ion-selective membranes through the liquid receiving openings using a pipet, etc., and a potential difference between both ion-selective electrodes is measured, thereby measuring the ion activity.

The device described in Japanese Patent Provisional Publication No. 58(1983)-211648 comprises plural pairs of ion-selective electrodes, which can determine ion activity of plural kinds of ions by only once spotting of a reference liquid and a liquid sample thereonto. The ion activity measuring device described in the above publication is characterized in that an ion-selective electrode sheet is arranged in such a manner that the ion-selective membrane is provided on the upper side An ion-selective electrode sheet generally comprises an electroconductive layer, a layer of water-insoluble salt, a layer of a water-soluble salt (sometimes not provided) and an ion-selective membrane laminated in this order on an insulating support. At the exposed portion (a portion exposed by necessity) of the electroconductive layer is provided an electricity-connecting region. The electricity-connecting region is brought into contact with a probe of a potential difference measuring device so as to determine the potential difference When the ion-selective membrane is placed on the upper side as disclosed in the above publication, the probe for measuring the potential difference and the electric wiring connected to the probe naturally are provided on the upper side of the ion-selective electrode sheet. The potential difference to be measured is so little that a head amplifier is desired to be arranged near the probe. Therefore, the head amplifier is required to be provided in the vicinity of the ion-selective electrode sheet. These electric parts occupy the upper space of the ion activity measuring device. On the other hand, a certain space at the upper portion of the ion activity measuring device is required for introduction of a reference liquid or a liquid sample by using a pipet. Therefore, the electric parts should be so arranged as not to disturb introduction of liquids. To meet with the requirement, the size of an automatic measuring device wherein an ion activity measuring device is automatically supplied so as to continuously measuring a plurality of samples becomes large.

In case that the electricity-connecting region is exposed with facing upward, the region and the vicinity of the region are apt to be stained with a liquid sample or a reference liquid supplied from the upper direction, thereby causing insufficient connection or insulation. Accordingly, there sometimes occurs errors in measurement of potential difference.

In measurement of ion activity, the area of an active surface of an ion-selective electrode (a surface of an ion-selective membrane) where liquids to be measured (a liquid sample and a reference liquid) are brought into contact is required to be unchanged within a certain range for securing the accuracy in measurement. In the ion-selective electrode sheet wherein a liquid sample is supplied to the upper surface of the sheet, means for defining the area where the liquid is supplied, for example, a mask provided with an opening is required In mass production of ion activity measuring devices, it is complicated and inefficient to produce a mask provided with an opening having accurate size and to arrange accurately the mask on the electrode sheet.

SUMMARY OF THE INVENTION

An object of the present invention is to solve the above mentioned three problems attached to the ion activity measuring device disclosed in Japanese Patent Provisional Pubilcation No. 58(1983)-211648 wherein the ion-selective electrode sheet is arranged in such a manner that the ion-selective membrane is provided on the upper side. Namely, the invention is to solve three problems, that is, occupation of upper space by the electric parts, stain of the electricity-connecting region and provision of a mask for defining the area where the liquid is supplied.

The present invention is provided to solve the above problems by providing an ion activity measuring device for measuring specific ion activity contained in a liquid sample comprising at least a pair of ion-selective electrode sheets which are electrically insulated from each other and selectively generate potential for a specific ion, liquid-guiding portions for guiding a liquid sample and a reference liquid to each active surface of said pair of electrode sheets respectively and a bridge for electrically connecting both liquid sample and reference liquid supplied on each electrode, which is characterized in that:

said each ion-selective electrode sheet is arranged in such a manner that the active surface of the ion-selective electrode is positioned on the lowest side;

said each liquid-guiding portion comprises a horizontal passage for conveying the liquid sample and the reference liquid supplied from the outside in the horizontal direction to the position just below the active surface of the ion-selective electrode, the horizontal passage being formed at a lower position than the active surface of the ion-selective electrode; and said horizontal passage is provided with a porous distributor in the form of a belt, which is bent to protrude upwardly from the horizontal passage to the position just below the active surface of the ion-selective electrode so that a liquid sample or a reference liquid conveyed to the porous distributor can be in contact with the active surface of the ion-selective electrode.

PREFERRED EMBODIMENTS OF THE INVENTION

The above object of the invention was effectively achieved by an embodiment wherein a water-impermeable middle frame is provided between said horizontal passage and said ion-selective electrode in such a manner that a space between the frame and the active surface of the ion-selective electrode is so determined as not to cause capillarity of a liquid sample or a reference liquid, and the frame is provided with an opening for permitting the porous distributor to protrude upwardly from the horizontal passage to the active surface of the ion-selective electrode.

One of the preferable embodiments of the ion activity measuring device of the invention comprises a top frame having a pair of opening portions for supplying a liquid sample or a reference liquid to the horizontal passage, a middle frame having a pair of opening portions corresponding to said pair of opening portions of the top frame, and a bottom frame having a groove for forming the horizontal passage, wherein at least a pair of said ion-selective electrode sheets are settled in the top frame.

The ion-selective electrode sheets which selectively generate potential for a specific ion are described in, for example, Japanese Patent Provisional Publication Nos. 58(1983)-156848, 58(1983)-193449, 58(1983)-211648, 60(1985)-237351, 60(1985)-237352, 61(1986)-7460, 61(1986)-7461 and 61(1986)-7462. The devices are well known to those skilled in the art. The ion-selective electrode generally comprises an insulating support, an electroconductive metal layer (e.g., silver layer), a layer of a water insoluble salt of said metal (e.g., silver chloride), an electrolytic layer containing a water soluble salt (e.g., potassium chloride, sodium chloride) consisting of the same anion and cation (e.g., potassium ion, sodium ion) as the anion of said water insoluble salt, and ion-selective membrane laminated in order.

Ion activity measurement is carried out by the use of a pair of ion-selective electrodes (half cell, preferably having the same structure) by the steps of: spotting both liquid sample and reference liquid onto an ion-selective membrane of each electrode, measuring the potential difference generated between the electroconductive metal layer of each electrode through a water retainable bridge which electrically connects the both liquids after a lapse of a certain time from the spotting, and calculating ion activity of the electrolyte contained in the liquid sample by using a calibration curve which is previously prepared. The above pair of ion-selective electrodes are required to be electrically insulated except at the bridged area As disclosed in Japanese Patent Provisional Publication No. 58(1983)-156848, the pair of ion-selective electrodes which are integrated on one support in the form of a sheet and electrically insulated by a scratched groove are advantageously used.

Provision of a scratched groove on a metal layer and a layer of insoluble salt of the metal (and sometimes on an ion-selective membrane) which are laminated on one support in the form of sheet is performed according to the method described in Japanese Patent Provisional Publication No. 60(1985)-24355.

The bridge for electrically connecting a liquid sample and a reference liquid spotted onto a pair of electrodes is preferably a porous bridge capable of using capillarity. The bridge preferably consists of natural fiber or synthetic polymer fiber (e.g., nylon fiber) and polyester fiber (e.g., polyethylene terephthalate fiber).

The ion activity measuring device of the invention is characterized in that the ion-selective electrode sheet is arranged in such a manner that the active surface of the ion-selective electrode is positioned on the lowest side. It is difficult to supply a liquid to be measured directly on the active surface by using a liquid measuring device such as a pipette under influence of force of gravity. Therefore, a liquid guiding portion having a horizontal passage for conveying a liquid sample or a reference liquid supplied from upper direction in the horizontal direction to the position just below the active surface of the ion-selective electrode is provided on a downside of the active surface of the ion-selective electrode. The horizontal passage usually is made of a liquid-impermeable insulating material in the form of a tub or cylinder having a tub in a portion.

The ion activity measuring device of the invention is characterized in that said horizontal passage is provided with a porous distributor in the form of a belt. The porous distributor can be made of a material having micropores continuously (porous) so as to generate capillarity (i.e., capillary action). Examples of the porous materials include a pharmacopoeial bandage, pharmacopoeial gauze, flax mosquito netting, lawn, silk gauze, filter paper, and synthetic polymer fiber (e.g., polyester fiber). Employment of nonwoven fabric (cloth) of a long filament of cellulose can give advantages that hemolysis of a blood sample hardly occurs, that cutting and molding processes are easily carried out, and that an applied liquid rapidly spreads. Therefore, nonwoven fabric of a long filament of cellulose is advantageously employed.

Among nonwoven fabrics of a long filament of cellulose, nonwoven fabric of cellulose spunbond substantially containing no binder is preferably used. Nonwoven fabric of long fiber of cotton linter is more preferably used. For example, nonwoven fabric prepared by using cotton linter solved in Schweitzer's liquid according to spun-bond method is advantageously employed. The thickness is preferably in the range of 100 to 500 $\mu$m.

These porous materials in the form of a belt are used by cutting suitably to give the structure of the measuring device. The structure of the device will be described referring to the attached drawings.

In the ion activity measuring device of the invention, the porous distributor is bent to protrude upwardly from the horizontal passage to just below the active surface of the ion-selective membrane so that a liquid sample or a reference liquid conveyed to the porous distributor can be in contact with the active surface of the electrode.

Figure 1:
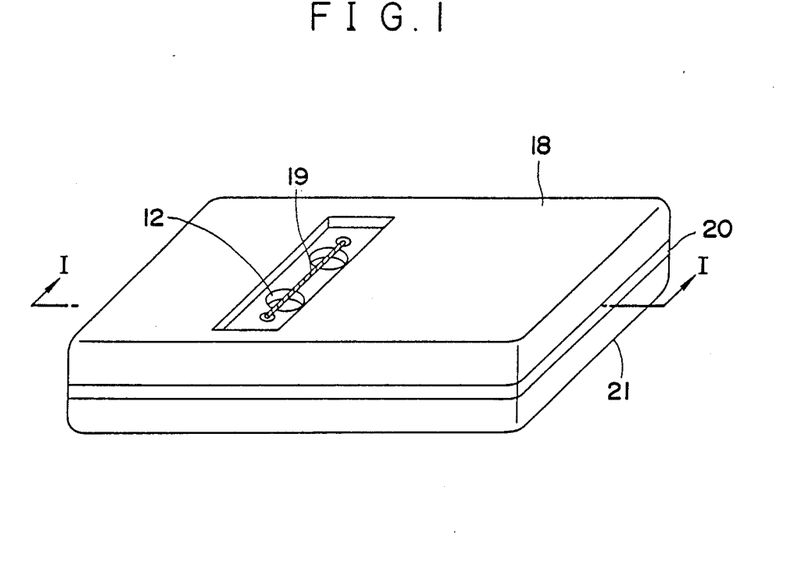
FIGS. 1 and 3 are perspective views illustrating an example of the invention.
Figure 2:
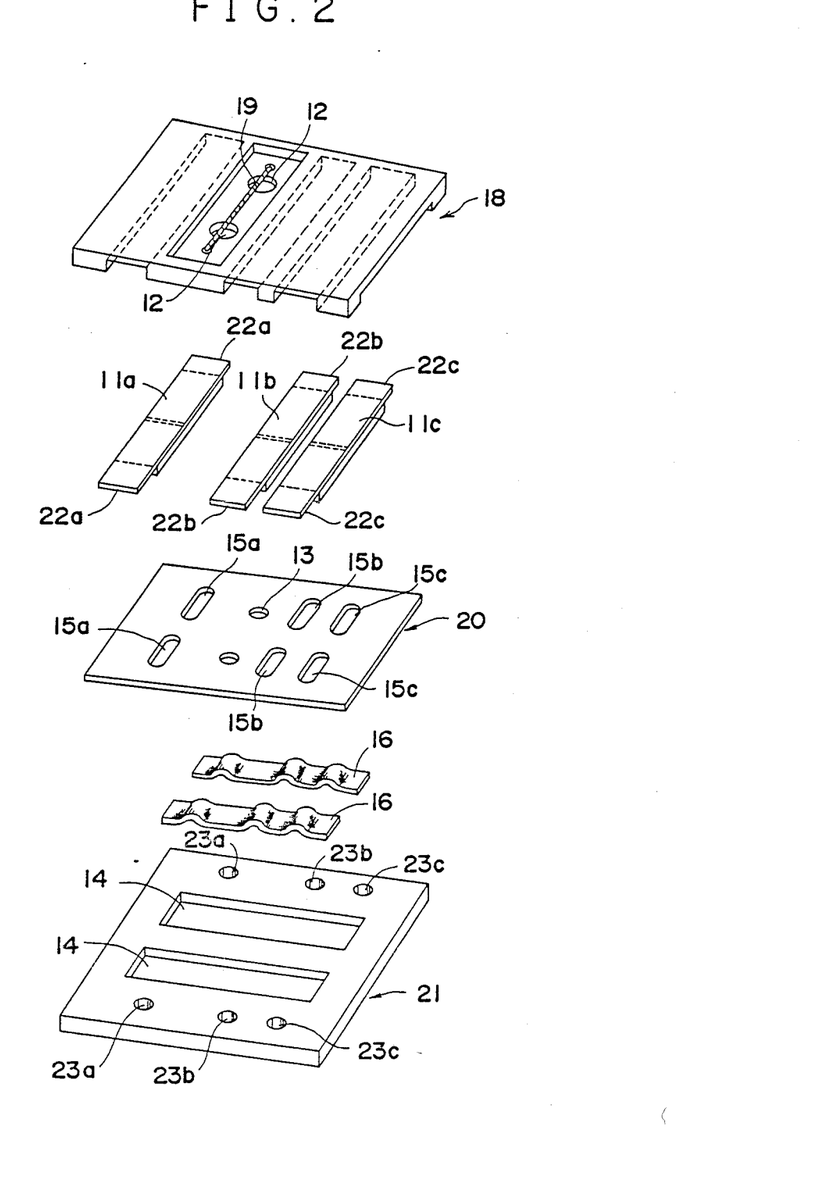
FIGS. 2 and 4 are sectional views of each member of the ion activity measuring device.

The above structure is produced by the following embodiments:

(1) Embodiment shown in FIGS. 1 and 2, wherein the porous distributor for conveying liquids is prepared by the steps of heating a thermoplastic synthetic polymer fiber such as polyester fiber at a suitable temperature not to lose the porosity, molding into a form of a distributor bent to protrude upward and fixing the distributor horizontally.

Figure 3:
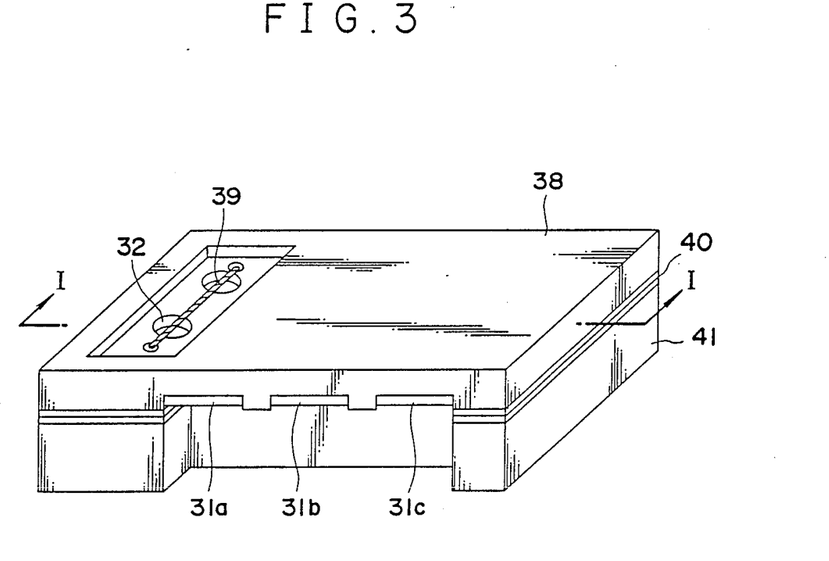
Figure 4:
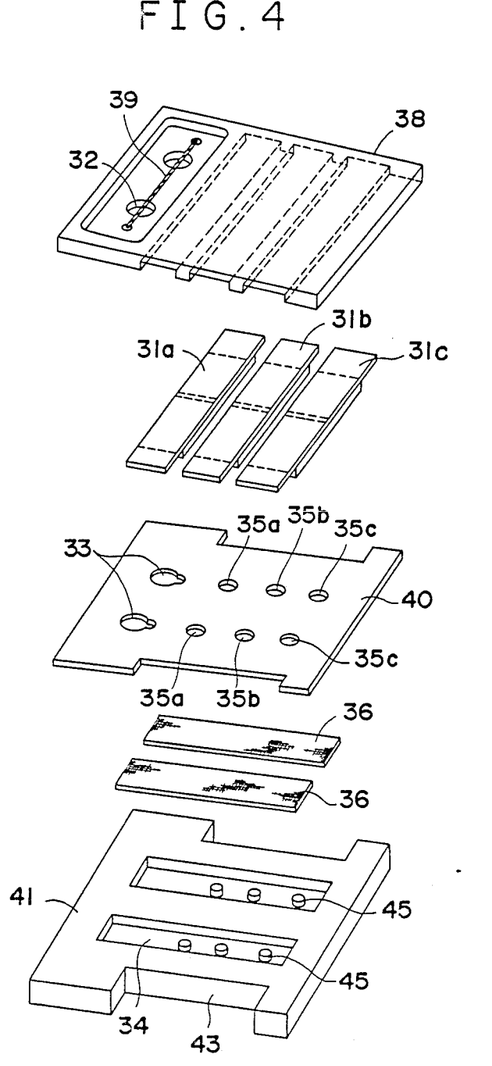

(2) Embodiment shown in FIGS. 3 and 4, wherein the components of the ion activity measuring device such as ion-selective electrode sheets and a porous distributor for conveying liquids are contained in a frame. In the embodiment, a protrusion is formed in a position facing the active surface of the ion-selective electrode sheet on the bottom of the groove formed on the bottom frame for receiving the porous distributor, so that the porous distributor for conveying liquids is kept bent to protrude to give an upward passage.

(3) Embodiment wherein a water-impermeable flat middle frame is provided between the horizontal passage and the ion-selective electrode in such a manner that a space between the middle frame and the active surface of the ion-selective electrode is so determined as to cause no capillarity of a liquid sample or a reference sample, an opening for allowing the porous distributor to protrude upward from the horizontal passage to just below the active surface of the ion-selective electrode, the porous distributor is inserted into the opening by force, thereby protruding to the ion-selective electrode and keeping the protruded condition by restoring force of the distributor.

In the ion activity measuring device of the invention, an additional member for conveying a liquid from the horizontal passage to the active surface of the ion-selective electrode is not required because the porous distributor is so provided. Therefore, the ion activity measuring device of the invention is easily produced. The porous distributor functions as both a member for conveying a liquid in the horizontal direction and a member for conveying a liquid to the active surface of the ion-selective electrode. Accordingly, a liquid sample and a reference liquid are conveyed smoothly, thereby shortening the time required for a liquid sample and a reference liquid to reach the active surface of the ion-selective electrode and rendering the time for contact of the liquid sample to the active surface uniform.

The ion activity measuring device of the invention will be described in more detail hereinafter by referring to the accompanying drawings.

Figure 1A:
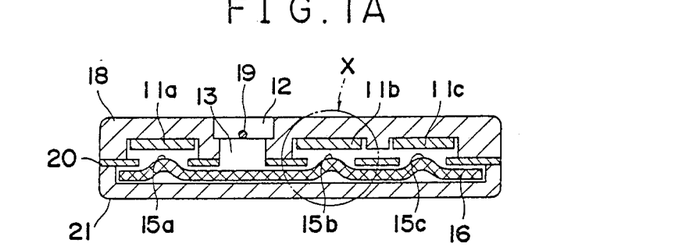
FIG. 1A and 3A are sectional views.
Figure 1B:
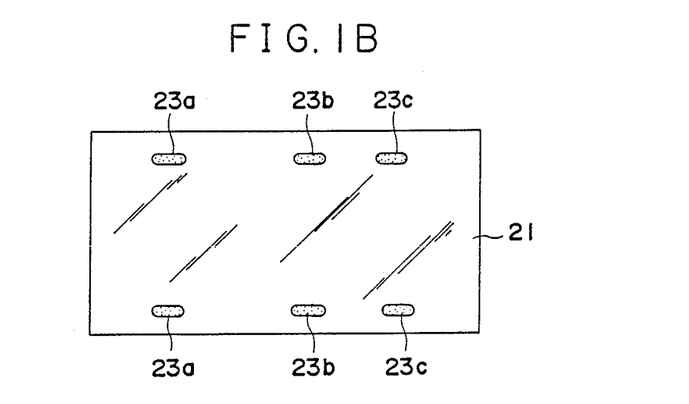
FIGS. 1B and 3B are bottom views.
Figure 1C:
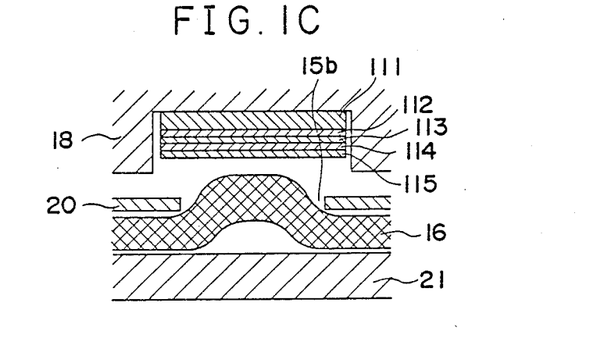
FIGS 1C and 3C are enlarged sectional views.

FIG. 1 is a perspective view illustrating an example of the ion activity measuring device according to the invention. FIG. 1A is an elevational section of the ion activity measuring device of FIG. 1 taken on line I—I; FIG. 1B is a bottom view of the ion activity measuring device of FIG. 1; and FIG. 1C is an enlarged view of a portion X enclosed with a circle in FIG. 1A. FIG. 2 shows each member of the ion activity measuring device of FIG. 1.

The ion activity measuring device shown in the above described figures comprises a top frame 18, three pairs of ion-selective electrodes 11a, 11b and 11c contained in the top frame, a bottom frame 21, a water-impermeable middle frame 20 provided between the top frame and bottom frame and a bridge 19.

The three pairs of ion-selective electrode sheets 11a, 11b and 11c are fixed in a groove provided on the top frame 18 made of a water-impermeable and insulating material such as polystyrene. Two openings 12 (one for supplying a liquid sample and the other for supplying a reference liquid) are formed on the top frame 18, and said two openings are traversed by a bridge 19 such as a combustible thread bridge of polyethylene terephthalate fiber to electrically separate both liquids from each other. Three pairs of ion-selective electrode sheets 11a, 11b and 11c comprise a combination of ion-selective electrodes which have the same structure and are electrically connected one another by the method disclosed in Japanese Patent Provisional Publication No. 58(1983)-156848. Ion-selective electrode sheets constituting each pair comprise a support 111 of insulating high polymer film, a metallic silver-deposited layer 112, a silver chloride layer 113, an electrolyte layer 114 and ion-selective membrane 115 laminated in this order as shown in FIG. 1C. The ion-selective electrode sheet having such structure is placed in the ion activity measuring device in such a manner that the ion-selective membrane 115 is upside down.

Between the top frame and the bottom frame is provided a middle frame 20 of water-impermeable material such as polyethylene. On the water-impermeable middle frame are provided four pairs of passages 13, 15a, 15b and 15c. There is no specific limitation with respect to the shape of these passages. The space between the water-impermeable middle frame 20 and the bottom surface of the ion-selective electrode sheet is, designed not to show capillarity of a liquid sample and a reference liquid. In order to keep the space, it is required to maintain the positional relationship between the ion-selective electrode and the middle frame. For this reason, both of the electrode and the middle frame are fixed to either top frame or bottom frame so that the electrode is placed at higher position than the middle frame. The electrode and middle frame may be fixed on either top or bottom frame after combining the electrode and middle frame The water-impermeable middle frame 20 is desired to be combined with the bottom surface of the top frame 18, with the upper surface of the bottom frame or with both of the surfaces by the use of an adhesive (e.g., pressure-sensitive adhesive, heat-sensitive adhesive, adhesive in the form of sheet) or through thermal bonding or physical engagement.

A bottom frame of thermoplastic resin (e.g., polystyrene) is arranged below the water-impermeable middle frame 20. The horizontal passage is formed in the bottom frame 21 as a groove 14. The groove 14 is equipped with the porous distributor 16 in the form of a belt. The porous distributor 16 is bent to upwardly protrude toward the ion-selective electrode at the position facing against the ion-selective electrode.

As understood from FIG. 1A, the liquid guiding portions for guiding a liquid sample and a reference liquid to each active surface of the ion-selective electrodes comprise openings 12 formed on the top frame, a downward passage 13 for conveying the spotted liquid to the horizontal passage provided on a position lower than the ion-selective electrode, a horizontal passage 14 for conveying the liquid in the horizontal direction to just below the ion-selective electrode, and the upward passages 15a, 15b and 15c for conveying the liquid in the upward direction to the active surface of the ion-selective electrode, that is, the surface of the ion-selective membrane. The horizontal passage 14 is formed on the bottom frame as a groove 14 and equipped with a porous distributor 16 in the form of a belt. The porous distributor 16 in the form of a belt is bent to upwardly protrude toward the ion-selective electrode at the passages 15a, 15b and 15c of the water-impermeable middle frame 20. In practice, the porous distributor 16 is inserted in the passages 15a, 15b and 15c from the bottom to the top (to the side of the electrode) and kept by the restoring force caused by elasticity of the porous distributor. The space between the top surface of the porous distributor 16 protruded from each passage and the bottom surface of the ion-selective electrode is determined in such a manner that both liquid sample and reference liquid conveyed to the distributor come into contact with the bottom surface of the ion-selective electrode. The porous distributor 16 protruded at each passage may be in contact with the bottom surface of the ion-selective electrode sheet. However, it is preferable for storage of the electrode that the distributor is not in contact with the bottom surface of the electrode until a liquid sample or a reference liquid is supplied to the distributor. To accomplish such a positional relationship between the distributor and the electrode sheet, the porous distributor preferably consists of a material which swells by absorbing a liquid sample or a reference liquid (e.g., 1.5 to several ten times).

The bottom frame has cutout portions 23a, 23b and 23c on the both sides to make each of the electricity-connecting regions 22a, 22b and 22c of the ion-selective electrodes 11a, 11b and 11c exposed in the downward direction. The cutout portions may be formed to correspond to the ion-selective electrodes respectively. Otherwise, one cutout portion may be formed for plural or all the ion-selective electrodes.

The operation of the ion activity measuring device shown in FIG. 1 will be described hereinbelow. A liquid sample and a reference liquid are respectively supplied using a pipette through the opening 12 formed on the top frame to the porous distributor 16 provided in the groove 14 of the bottom frame. The liquid sample and the reference liquid are electrically connected by the bridge 19 provided across the opening. Each liquid is conveyed in the horizontal passage 14 to just below the ion-selective electrode through the porous distributor 16. The porous distributor 16 is bent at the positions corresponding to the passages 15a, 15b, 15c of the water-impermeable middle frame 20 so as to upwardly protrude toward the ion-selective electrode. When the liquid is conveyed in the porous distributor 16 to reach just below the ion-selective electrodes, the distributor which absorbed the liquid swells to come into contact with the active surface of the ion-selective electrodes 11a, 11b, 11c, that is, the ion-selective membranes of the ion-selective electrodes. Thus, a potential difference is generated between each pair of ion-selective electrodes by the liquid sample and the reference liquid. The potential difference can be measured by a potentiometer connected to the electricity-connecting regions 22a, 22b, 22c of the pairs of the ion-selective electrodes 11a, 11b, 11c. Since the liquid sample and the reference liquid cause no capillary action at the space between the water-impermeable middle frame 20 and the bottom surface of the ion-selective electrode, the liquid is supplied to the surface of the electrode through the porous distributor when the distributor comes into contact with the bottom surface of the ion-selective electrode or comes so near as to generate capillarity. Therefore, the area of the surface of the electrode where the liquid comes into contact is well defined, and reproduction of the measurement is satisfactory.

Figure 3A:
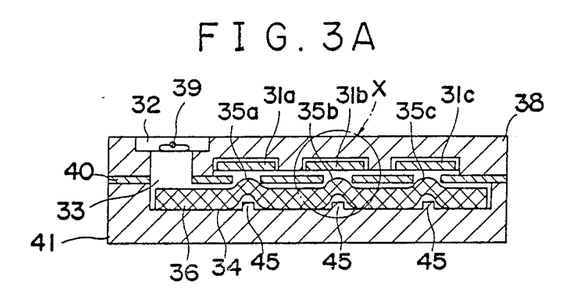
Figure 3B:
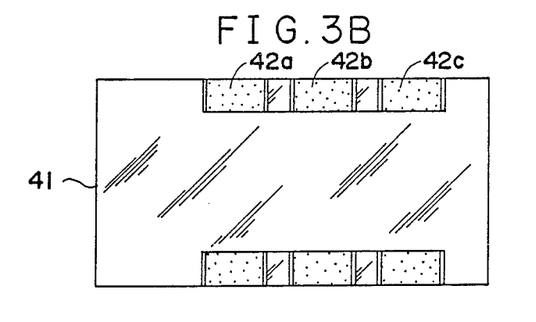
Figure 3C:
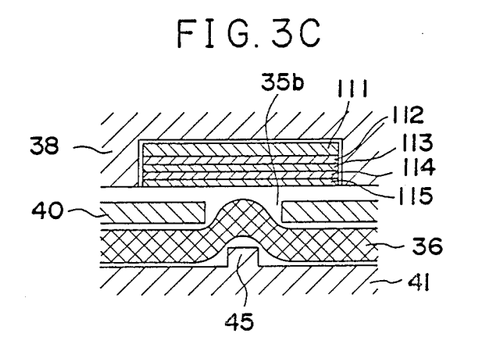

FIG. 3 is a perspective view showing another embodiment of the ion activity measuring device according to the invention. FIG. 3A is an elevational section of the ion activity measuring device of FIG. 3 taken along line I'—I', FIG. 3B is a bottom view of the ion activity measuring device of FIG. 3 and FIG. 3C is an enlarged view of a portion X enclosed with a circle in the FIG. 3A. FIG. 4 separately shows each member of the ion activity measuring device of FIG. 3.

The ion activity measuring device shown in these figures comprises a top frame 38, three pairs of ion-selective electrodes 31a, 31b, 31c arranged in the frame, a bottom frame 41, water-impermeable middle frame 40 provided between the top frame and bottom frame, and a bridge 39.

The three pairs of ion-selective electrode sheets 31a, 31b, 31c are settled in the groove of the polyethylene top frame 38 and fixed to the frame. The top frame 38 has two liquid-receiving openings 32 (one for a liquid sample and the other for a reference liquid). These openings are traversed by a bridge 39 made of, for example, polyethylene terephthalate fiber to electrically connect both a reference liquid and liquid sample to each other. The three pairs of ion-selective electrode sheets 31a, 31b, 31c comprise a combination of the same ion-selective electrode sheets as those electrically connected by the method disclosed in Japanese Patent Provisional Publication No. 58-156848. Each pair of ion-selective electrode sheets comprise a support 111 of insulating high polymer film, metallic silver-deposited layer 112, a silver chloride layer 113, an electrolyte layer 114 and an ion-selective membrane 115, laminated in order in the same manner as the ion-selective electrode sheets 11a, 11b and 11c, as shown in FIG. 1C. In the measuring device, the ion-selective electrode sheets are arranged in such a manner that the ion-selective membranes are placed upside down.

Between the top frame and the bottom frame is provided a middle frame 40 made of a water-impermeable material such as polyethylene. Four pairs of passages 33, 35a, 35b, 35c are formed on the water-impermeable middle frame 40. It is desired that there causes no capillarity of a liquid sample and a reference liquid in the space between the water-impermeable middle frame 40 and the ion-selective electrode sheets. The water-impermeable middle frame 40 is desired to be combined with the top surface of the bottom frame 41 or with the bottom surface of the top frame 38 by the use of an adhesive (e.g., pressure-sensitive adhesive, heat-sensitive adhesive, adhesive in the form of sheet) or through thermal bonding or physical engagement.

The bottom frame 41 of thermoplastic resin (e.g., polystyrene) is arranged below the water-impermeable middle frame 40. The horizontal passage is formed in the bottom frame 41 as a groove 34. The groove 34 is equipped with the porous distributor 36. The porous distributor is bent to protrude toward the ion-selective electrode by a protrusion 45 formed on the bottom of the groove 34. The same principle as described regarding the embodiment shown in FIG. 1 can be applied to this embodiment with respect to the space between the bottom surface of the ion-selective electrode sheet and the top surface of the protruded portion of the porous distributor kept by the protrusion.

As understood from FIG. 3A, the liquid supplying portions comprise an opening 32 formed on the top frame, downward passage 33 for conveying the spotted liquid to the horizontal passage provided at a position lower than the ion-selective electrode, a horizontal passage 34 for conveying the liquid in the horizontal direction to just below the ion-selective electrode and the upward passages 35a, 35b, 35c for conveying the liquid in the upper direction to the active surface of each ion-selective electrode, that is, the surface of the ion-selective membrane. The horizontal passage 34 is formed on the bottom frame as a groove. The porous distributor 36 in the form of a belt settled in the passage is bent by a protrusion 45 provided at the bottom of the groove 34 so as to protrude toward the ion-selective electrode at a position corresponding to the passages 35a, 35b, 35c of the water-impermeable middle frame 40.

The bottom frame has cutout portions 43 on the both sides to make each of the electricity-connecting regions 42a, 42b, 42c of the ion-selective electrodes 31a, 31b, 31c exposed in the downward direction. The cutout portions may be formed to correspond to the ion-selective electrodes respectively. Otherwise, one cutout portion may be formed for plural or all the ion-selective electrodes.

The operation of the ion activity measuring device shown in FIG. 3 will be described hereinbelow. A liquid sample and a reference liquid are respectively supplied from the opening 32 formed on the top frame to the porous distributor 36 provided in the groove 34 of the bottom frame through the passage 33 by using a pipette or a divider. The liquid sample and the reference liquid are electrically connected by the bridge provided across the opening. Each liquid is conveyed in the horizontal passage 34 to just below the ion-selective electrode through the porous distributor 36. The porous distributor 36 is bent at the positions corresponding to the passages 35a, 35b and 35c of the water-impermeable middle frame 40 by the protrusion 45 formed on the bottom of the groove 34 so as to upwardly protrude toward the ion-selective electrode. When the liquid is conveyed in the porous distributor 36 to just below the ion-selective electrode, the distributor absorbs the liquid and swells to come into contact with the active surface of each ion-selective electrode, that is, the surface of each ion-selective membrane. Thus, a potential difference is generated between each pair of ion-selective electrodes by the liquid sample and reference liquid. The potential difference can be measured by a potentiometer connected to the electricity-connecting regions 42a, 42b, 42c of the pairs of ion-selective electrodes 31a, 31b, 31c.

In both embodiments of FIGS. 1 and 3, the top frame and the bottom frame may be combined directly or through the water-impermeable middle frame. The frames are directly combined in the same manner as when the frames are combined through the water-impermeable middle frame. Each of the top frame, bottom frame and water-impermeable middle frame is not necessarily an integrated form and can be composed of plural members, as far as the porous distributor and the ion-selective electrode can be contained therein.

Each of the top frame, water-impermeable middle frame and bottom frame can be prepared using a desired self-supporting material. From viewpoints of various properties such as insulating properties, moldability and shock impact resistance, these frames are preferably formed from plastic materials. For instance, these frames can be formed by known methods such as a molding method using a plastic material and a desired mold or a drawing method using a plastic sheet.

Around the opening 12 is provided a protruded region which serves to prevent the liquid from flowing over the opening and also serves to easily spot the liquid without fail.

As the material employable for the bridge, there can be mentioned a membrane filter, a conventional filter paper and a filter paper laminated with hydrophobic organic polymer layers on the both sides as described in Japanese Patent Provisional Publication No. 55(1980)-20499.

In measurement of ion activity of a liquid sample by employing the ion activity measuring device of the invention, it is desired to supply a liquid sample and a reference liquid to a liquid receiving opening (e.g., the opening 12 in FIG. 1 and the opening 32 in FIG. 3) in a predetermined amount by a pipette or a divider. However, the accuracy of the amount is not so strictly demanded. The liquid to be measured (a liquid sample and a reference liquid) is conveyed from the opening to the active surface of each ion-selective electrode through the porous distributor. Since the volume of the liquid guiding portion is limited, the liquid spreads against surface tension from the liquid guiding portion, for example, the opening provided just below the electrode, when excessive amount of the liquid is supplied. Therefore, the area of the electrode where the liquid contacts is increased, thereby lowering accuracy of the measurement.

When the amount of the liquid is too little, the liquid only spreads over a part of the porous liquid distributor and sufficient amount of the liquid is not conveyed to the electrode located far from the liquid guiding portions.

In case that the excessive amount of the liquid is supplied, the distribution of the liquid between the electrodes is not uniform. But, high accuracy in the amount of the liquid is not desired as far as the above mentioned troubles are not caused (e.g., ±25%).

Pipets disclosed in Japanese Patent Provisional Publication Nos. 61(1986)-173131, 61(1986)-198036, 60(1985)-274710 and 60(1985)-279840 are suitably employable in the invention.

We claim:

1. A device for measuring ion activity in a liquid sample comprising at least a pair of ion-selective electrode sheets which are electrically insulated from each other and selectively generate potential for a specific ion, liquid-guiding portions for guiding a reference liquid and a liquid sample to each active surface of said pair of ion-selective electrode sheets respectively, and a bridge for electrically connecting both liquids supplied on the electrode sheets to each other, wherein:

said each ion-selective electrode sheet is arrange in such a manner that the active surface of the ion-selective electrode is placed upside down;

said each liquid guiding portion comprises a horizontal passage for conveying said liquid sample or said reference liquid supplied from the outside in the horizontal direction to the position just below the active surface of the ion-selective electrode, the horizontal passage being formed in a lower position than the active surface of the ion-selective electrode; and said horizontal passage is provided with a swellable porous distributor in the form of a belt and having deformations therein which protrude upwardly, said deformations being positioned at a spaced-apart distance from the active surface from the ion-selective electrode, such that when a sample liquid or reference liquid is introduced to the porous distributor, the deformations swell upwardly such as to bring the deformed portion of the liquid distributor and the liquid which it contains into contact with the active surface of the ion-selective electrode.

2. The ion activity measuring device as claimed in claim 1, wherein a water-impermeable flat middle frame having an opening for allowing the porous distributor to protrude upwardly from the horizontal passage to the active surface of the ion-selective electrode is provided between said horizontal passage and said ion-selective electrode.

3. The ion activity measuring device as claimed in claim 2, comprising: a top frame having a pair of openings for supplying a liquid sample and a reference liquid from the outside to the horizontal passage; said water-impermeable middle frame having a pair of openings leading to said pair of openings of the top frame and said opening; and a bottom frame having a groove for forming said horizontal passage,
wherein at least a pair of said ion-selective electrode sheets are settled in said top frame.

4. The ion activity measuring device as claimed in claim 3, wherein a protrusion for protruding said porous distributor to a position just below the active surface of the ion-selective electrode is provided in the groove of said bottom frame.

5. The ion activity measuring device as claimed in claim 1, wherein said porous distributor consists essentially of a long filament of cellulose.

6. The device of claim 1 wherein the horizontal passage and surface of the ion-selective electrode are spaced apart sufficiently to avoid contact of a reference or sample liquid in said horizontal passage with the surface of the ion-selective electrode due to capillary action.

* * * * *